United States Patent
Stodola et al.

(10) Patent No.: US 12,427,250 B2
(45) Date of Patent: Sep. 30, 2025

(54) SYSTEM AND METHOD FOR EXTENDING THE STORAGE DURATION OF A RECHARGEABLE BATTERY OF AN INFUSION PUMP

(71) Applicants: Baxter International Inc., Deerfield, IL (US); Baxter Healthcare SA, Glattpark (CH)

(72) Inventors: David Scott Stodola, Arlington Heights, IL (US); Mark Andrew Luzbetak, Kildeer, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 907 days.

(21) Appl. No.: 17/523,285

(22) Filed: Nov. 10, 2021

(65) Prior Publication Data

US 2022/0143315 A1    May 12, 2022

Related U.S. Application Data

(60) Provisional application No. 63/112,005, filed on Nov. 10, 2020.

(51) Int. Cl.
*A61M 5/172*    (2006.01)
*G06F 1/3212*    (2019.01)
(Continued)

(52) U.S. Cl.
CPC ........... *A61M 5/172* (2013.01); *G06F 1/3212* (2013.01); *H02J 7/00032* (2020.01);
(Continued)

(58) Field of Classification Search
CPC ........... A61M 5/172; A61M 2205/502; A61M 2205/8212; G16H 20/17; G16H 40/40;
(Continued)

(56) References Cited

U.S. PATENT DOCUMENTS

| | | | |
|---|---|---|---|
| 2008/0215039 A1* | 9/2008 | Slatkine | A61M 5/425 606/9 |
| 2008/0243079 A1 | 10/2008 | Wooley et al. | |
| 2010/0084918 A1* | 4/2010 | Fells | H02J 7/00045 307/32 |
| 2011/0063094 A1* | 3/2011 | Meiertoberens | A61M 5/14244 340/12.5 |
| 2012/0327749 A1* | 12/2012 | Tsukamoto | G06F 1/3212 368/204 |
| 2016/0020624 A1* | 1/2016 | Chang | H02J 9/002 320/136 |

(Continued)

FOREIGN PATENT DOCUMENTS

CN    210897531 U  *  6/2020

OTHER PUBLICATIONS

International Search Report and Written Opinion for Appln No. PCT/US2021/058731 dated Feb. 16, 2022.

*Primary Examiner* — Jerry D Robbins
(74) *Attorney, Agent, or Firm* — K&L Gates LLP

(57) ABSTRACT

A method for extending the storage lifetime of a battery located in a device is disclosed. The battery lifetime extension method includes providing a device that derives its power from a rechargeable battery. The method further includes providing a rechargeable battery that is capable of communicating with the device. When the device is powered off by a user, a computer implemented program utilized by the device communicates with the battery and automatically powers up the device into a lower power mode upon expiration of a variable duration timer monitored by the computing unit that continuously repeats according to the programed duration cycle, evaluates the state of charge of the rechargeable battery, determines whether the state of charge of the rechargeable battery is above or below a variable programed threshold, and communicates a command to the rechargeable battery to remain in a low power state until a charge is applied to the rechargeable battery.

20 Claims, 3 Drawing Sheets

(51) Int. Cl.
  *H02J 7/00* (2006.01)
  *G16H 20/17* (2018.01)
  *G16H 40/40* (2018.01)

(52) U.S. Cl.
  CPC .......... *H02J 7/0048* (2020.01); *H02J 7/0063* (2013.01); *H02J 7/0071* (2020.01); *H02J 7/007182* (2020.01); *A61M 2205/502* (2013.01); *A61M 2205/8212* (2013.01); *G16H 20/17* (2018.01); *G16H 40/40* (2018.01)

(58) Field of Classification Search
  CPC ..... G06F 1/3212; H02J 7/0048; H02J 7/0063; H02J 7/007182
  See application file for complete search history.

(56) References Cited

U.S. PATENT DOCUMENTS

| | | | |
|---|---|---|---|
| 2016/0081018 A1* | 3/2016 | Macours | H04M 1/6016 455/574 |
| 2016/0089999 A1* | 3/2016 | Tabatowski-Bush | H02J 7/0016 320/136 |
| 2016/0227598 A1* | 8/2016 | Singh | H04W 76/18 |
| 2016/0347426 A1 | 12/2016 | Thompson et al. | |
| 2018/0126067 A1* | 5/2018 | Ledford | A61M 5/172 |
| 2019/0328964 A1* | 10/2019 | Desch | A61M 5/1456 |
| 2021/0060249 A1* | 3/2021 | Golenberg | A61M 5/1723 |
| 2021/0146045 A1* | 5/2021 | Golenberg | G16H 20/17 |
| 2021/0178063 A1* | 6/2021 | Parikh | G06V 40/23 |
| 2021/0178064 A1* | 6/2021 | Vleugels | G16H 20/17 |
| 2022/0069365 A1* | 3/2022 | Ingurthi | H02J 7/007182 |

\* cited by examiner

SYSTEM AND METHOD FOR EXTENDING THE STORAGE DURATION OF A RECHARGEABLE BATTERY OF AN INFUSION PUMP

PRIORITY CLAIM

This application claims priority to and the benefit as a non-provisional application of U.S. Provisional Patent Application No. 63/112,005, filed Nov. 10, 2020, the entire contents of which are hereby incorporated by reference and relied upon.

BACKGROUND

In general, some patients may require a medical treatment that includes a precise delivery of either continuous medication or medication at set periodic intervals. Medical pumps have been developed to provide controlled drug infusion. The known medical pumps administer drugs and other fluids at a precise rate that keeps a drug concentration of a patient within a therapeutic margin and out of an unnecessary or possibly toxic range. Basically, the medical pumps provide appropriate drug delivery to a patient at a controllable rate, which does not require frequent attention.

Medical pumps may facilitate administration of intravenous therapy to patients both in and outside of a clinical setting. Outside a clinical setting, doctors have found that in many instances patients can return to substantially normal lives, provided that they receive periodic or continuous intravenous ("IV") administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusion of drugs in solution over relatively short periods such as from 30 minutes to multiple hours. These conditions and others have combined to promote the development of increasingly lightweight, portable, or ambulatory infusion pumps that can be worn by a patient and are capable of administering a continuous supply of medication at a desired rate or providing several doses of medication at scheduled intervals.

Configurations of infusion pumps include elastomeric pumps, which squeeze solution from flexible containers, such as balloons, into IV tubing for delivery to a patient. Alternatively, spring-loaded pumps pressurize solution containers or reservoirs. Certain pump designs utilize cartridges containing flexible compartments that are squeezed by pressure rollers to discharge solutions. Infusion pumps utilizing syringes are also known where a drive mechanism moves a plunger of the syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

Additionally, some infusion pumps are portable. For example, an infusion pump may be smaller and more compact for mobile use by ambulatory patients or other patients. Naturally, a portable pump must be supplied with an equally portable power source as a means for powering a pump motor. Batteries are a suitable choice of power for portable units. Some pumps may use disposable batteries while other pumps may use rechargeable batteries. The pump may also be sized to be attached to an IV pole. The IV pole, with attached pump, may remain stationary or may be moved about in a hospital setting. In another example, the pump may be attached to a hospital bed or other support structure. As noted above, the pump may be portable and may be carried on a patient, for example, in a pouch. The pump may be attached to and supported by the patient's clothing and/or other support apparel such as a belt, a vest, or the like.

As noted above, rechargeable batteries are widely used as a power source for various types of systems, such as infusion pumps. The longevity of a battery stored in a system is a critical factor to the performance of that system. However, rechargeable battery longevity is reduced when a battery pack is damaged due to the cell(s) being discharged to below a voltage threshold which can be recharged safely. This over-discharge can occur during active use or while being stored. Mitigating the damage to the battery pack can be achieved by ensuring the cell voltage does not drop below a certain threshold. Monitoring cell voltage of a rechargeable battery in a system can be done either actively or passively. Additionally, the method of ensuring the cell voltage of a battery stored in a system does not drop below a certain threshold can be an active process (requiring user intervention or mechanical additions) or passive process (the system itself executes a process to maintain cell voltage).

Several methods exist to protect batteries stored in systems from being damaged by low cell voltage, thereby extending storage lifetime of the battery. However, the existing methods each have disadvantages. For example, one existing method for protecting a battery pack stored in a system from being damaged by a low cell voltage is to require the user of the system to simply remove the battery pack from the system. This method, however, presents several logistical concerns such as the battery pack being misplaced, and the system being damaged by improperly removing or reattaching the battery pack by the user. Additionally, another existing method for protecting a battery pack stored in a system from being damaged by a low cell voltage is to add a mechanical switch to the system to disconnect the battery completely from the system. This method prevents the system from executing passive actions, such as self-initiated restarting, because the battery pack is mechanically disconnected from the system and cannot power the system. Further drawbacks of this method are manifested in performance issues depending on the battery manager load inside the battery pack. Finally, smart battery packs that automatically shut down when the batteries are fully depleted have been implemented to mitigate the damage caused by low cell voltage on a battery pack. However, current implementations of smart battery packs provide insufficient storage duration since the threshold is fixed instead of being variable based on use case.

Accordingly, a method and system for extending the storage duration of a rechargeable battery in a system that does not require user intervention is desired.

SUMMARY

The present disclosure provides a new and innovative method and system for extending the storage duration of a rechargeable battery. In various embodiments, the device storing the rechargeable battery is an infusion pump. The infusion pump in various embodiments is a peristaltic pump, a syringe pump, or an ambulatory pump configured to deliver a medication to a patient. It should be appreciated that the device may be any type of medical device, or any other suitable device having a rechargeable battery.

The provided method includes utilizing software run by the device to monitor the state of the device and the state of the battery stored in the device. When the device is not in use and the battery state of charge ("SOC") is below a threshold, the device communicates with the battery manager and commands the battery to shut down its output and enter a low power state. SOC is the percentage of the remaining capacity divided by the full charge capacity of the battery and is an indicator of potential storage duration. The frequency of the SOC query to determine whether the SOC is above or below a threshold is variable. The query can be initiated by a programmed periodic timer expiring. The SOC threshold at which the device enters a lower power state can be variable or fixed. Once the battery is in the shut-down state, the device only operates after a charge has been applied to the battery stored in the device.

It has been shown that monitoring SOC and ensuring the battery cell voltage does not drop below a certain SOC threshold, decreases the likelihood of the battery being damaged from over-discharge during storage. As a result of periodic monitoring and directing the battery into a low power state, the storage duration of a battery in a device is significantly increased.

In light of the disclosure herein and without limiting the disclosure in any way, in a first aspect of the present disclosure, which may be combined with any other aspect listed herein, a battery control method for extending the storage lifetime of a rechargeable battery in a device includes providing a device that derives its power from a rechargeable battery, wherein the device includes a computing unit capable of executing a computer implemented program. The method also includes providing a rechargeable battery that is capable of storing energy wherein the rechargeable battery is further capable of communicating with the device the rechargeable battery is powering. The method further includes deploying a computer implemented program on the device in which the computing unit of the device commands the rechargeable battery to enter a lower power state upon the device being manually powered down by user. Additionally, the method includes automatically powering up the device into a low power mode upon expiration of a variable duration timer which triggers the computing unit and continuously repeats according to a programed duration cycle, evaluating the state of charge of the rechargeable battery by the battery and/or computing unit, and determining whether the remaining capacity of the rechargeable battery is above or below a variable programed threshold. The method includes communicating a command to the rechargeable battery to remain in an off or low power state until a charge is applied to the rechargeable battery upon determining the remaining capacity of the rechargeable battery is below the programed threshold. The method may also include waking the device and rechargeable battery upon detection of an alternate power source. The method further repeatedly determines the remaining capacity of the rechargeable battery upon expiration of the programed timer.

In a second aspect of the present disclosure, which may be combined with any other aspect listed herein, the variable duration timer has a predetermined length that is 12 hours.

In a third aspect of the present disclosure, which may be combined with any other aspect listed herein, the variable duration timer has a predetermined length that between thirty minutes and 48 hours.

In a fourth aspect of the present disclosure, which may be combined with any other aspect listed herein, the variable programed threshold is 3.0 watt-hours ("Wh").

In a fifth aspect of the present disclosure, which may be combined with any other aspect listed herein, the variable programed threshold is between 0.5 Wh and 6.0 Wh.

In a sixth aspect of the present disclosure, which may be combined with any other aspect listed herein, the method further includes detecting, via the computing unit, that at least one of the cells of the rechargeable battery is below a minimum cell voltage, and causing the rechargeable battery to disable.

In a seventh aspect of the present disclosure, which may be combined with any other aspect listed herein, the minimum cell voltage is −1.9 Wh of remaining capacity of the rechargeable battery.

In an eighth aspect of the present disclosure, which may be combined with any other aspect listed herein, an apparatus with battery control for extending the storage lifetime of a rechargeable battery includes a rechargeable battery having one or more battery cells, a user interface, and a computing unit communicatively coupled to the user interface and the rechargeable battery. The computing unit is configured to execute a computer implemented program that causes the computing unit to command the rechargeable battery to enter a lower power state after receiving a command via the user interface to manually power down, automatically power into a low power mode upon expiration of a variable duration timer which triggers the computing unit and continuously repeats according to a programed duration cycle, evaluate a state of charge of the rechargeable battery, determine whether the remaining capacity of the rechargeable battery is above or below a variable programed threshold, communicate a command to the rechargeable battery to remain in an off or low power state until a charge is applied to the rechargeable battery after determining the remaining capacity of the rechargeable battery is below the programed threshold, wake the rechargeable battery after detection of an alternate power source, and repeatedly determine the remaining capacity of the rechargeable battery after expiration of the programed timer.

In a ninth aspect of the present disclosure, which may be combined with any other aspect listed herein, the rechargeable battery, the user interface, and the computing unit are part of a peristaltic pump, a syringe pump, or an ambulatory pump.

In a tenth aspect of the present disclosure, which may be combined with any other aspect listed herein, the variable duration timer has a predetermined length that between thirty minutes and 48 hours.

In an eleventh aspect of the present disclosure, which may be combined with any other aspect listed herein, the variable programed threshold is between 0.5 Wh and 6.0 Wh.

In a twelfth aspect of the present disclosure, which may be combined with any other aspect listed herein, the computer implemented program is further configured to cause the computing unit to detect that at least one of the cells of the rechargeable battery is below a minimum cell voltage, and cause the rechargeable battery to disable.

In a thirteenth aspect of the present disclosure, which may be combined with any other aspect listed herein, the minimum cell voltage is −1.9 Wh of remaining capacity of the rechargeable battery.

In a fourteenth aspect of the present disclosure, which may be combined with any other aspect listed herein, the computing unit manages a device active state that consumes 4 W, the low power mode consumes 30 mW, and the off or low power state consumes 250 uW.

In a fifteenth aspect of the present disclosure, which may be combined with any other aspect listed herein, the off or low power state is a battery shutdown state.

In a sixteenth aspect of the present disclosure, which may be combined with any other aspect listed herein, the computer implemented program is configured to at least double a storage life of the rechargeable battery using the variable duration timer and by placing the rechargeable battery into the off or low power state after determining the remaining capacity of the rechargeable battery is below the programed threshold.

In a seventeenth aspect of the present disclosure, which may be combined with any other aspect listed herein, an apparatus with battery control for extending the storage lifetime of a rechargeable battery includes a user interface and a computing unit communicatively coupled to the user interface and a rechargeable battery. The computing unit is configured to execute a computer implemented program that causes the computing unit to command the rechargeable battery to enter a lower power state after receiving a command via the user interface to manually power down, automatically power into a low power mode upon expiration of a variable duration timer which triggers the computing unit and continuously repeats according to a programed duration cycle, evaluate a state of charge of the rechargeable battery, determine whether the remaining capacity of the rechargeable battery is above or below a variable programed threshold, communicate a command to the rechargeable battery to remain in an off or low power state until a charge is applied to the rechargeable battery after determining the remaining capacity of the rechargeable battery is below the programed threshold, wake the rechargeable battery after detection of an alternate power source, and repeatedly determine the remaining capacity of the rechargeable battery after expiration of the programed timer.

In an eighteenth aspect of the present disclosure, which may be combined with any other aspect listed herein, the user interface and the computing unit are part of a peristaltic pump, a syringe pump, or an ambulatory pump.

In a nineteenth aspect of the present disclosure, which may be combined with any other aspect listed herein, the variable duration timer has a predetermined length that between thirty minutes and 48 hours, and the variable programed threshold is between 0.5 Wh and 6.0 Wh.

In a twentieth aspect of the present disclosure, which may be combined with any other aspect listed herein, the computer implemented program is further configured to cause the computing unit to detect that at least one of the cells of the rechargeable battery is below a minimum cell voltage and cause the rechargeable battery to disable.

In a twenty-first aspect of the present disclosure, any of the structure and functionality disclosed in connection with FIG. 2 may be combined with any of the other structure and functionality disclosed in connection with FIG. 3.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

The present disclosure provides a method for extending the lifetime of a rechargeable battery stored in a device. The provided method combines the benefits of passive battery management and the flexibility of computer implemented programs to arrive at a novel method for extending the longevity of a rechargeable battery stored in a device.

The disclosed method provides an extended duration of storage in a device without requiring the end user to perform any manual actions or separating the battery from the device while still allowing the device to turn on remotely, based on timers, or other electronic methods before the battery has too little energy to provide significant time of use. Since the device is disabled only when not in use and the battery is nearly depleted at the time this event is triggered, the device's battery run time is not affected.

Figure 1:
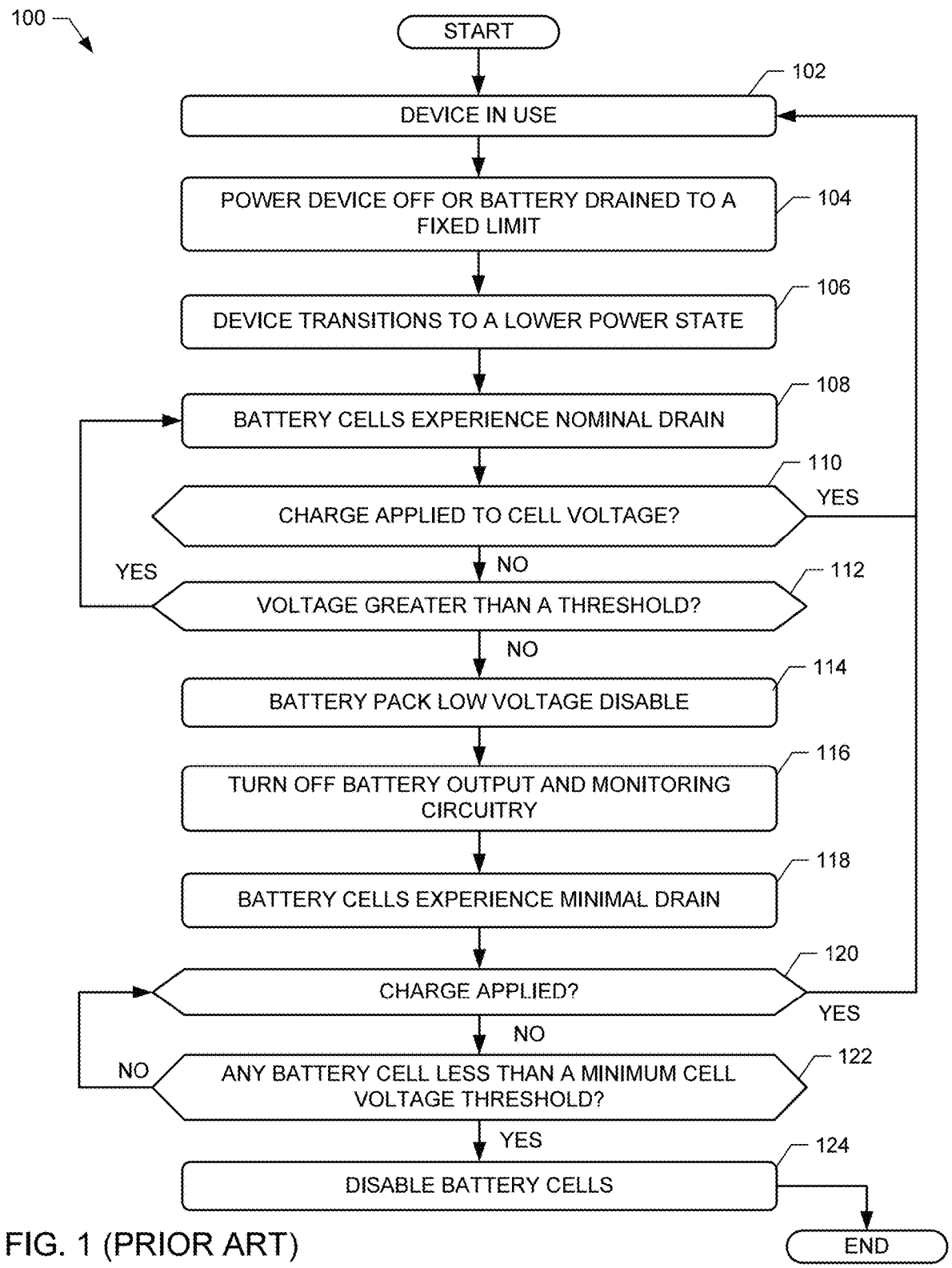
FIG. 1 is a flow chart illustrating a currently known method for extending battery storage life.

FIG. 1 is a flow chart illustrating a currently known method 100 for extending battery lifetime. While the device storing the rechargeable battery is in use, at any time, the user may manually power down the device by pressing the power button. Even though the device is in a low power state, there is still drain on the cells. The battery drain comes from the device and battery manager electronics in the battery pack in addition to minimal drain due to battery cell self-discharge. A battery manager integrated circuit monitors battery pack parameters including current, cell, and pack voltages.

The battery manager integrated circuit continually monitors the cell and pack voltages as well as currents and determines the instantaneous and capacity remaining in the cells in addition to other parameters. These parameters can be queried from the battery monitor by the device at any time while the battery monitor is on. In this typical application, the method 100 begins when the device is in use (block 102). Typically, a user will operate the device when there is a sufficiently high state of charge. For example, the user operates the device when the state of charge is greater than 20%. Next, the user powers off the device or the device drains the battery to a fixed limit that causes the device to power off (block 104). At this point, the device transitions to a low power state (block 106). At this state, the device can be powered on by the user still using battery power.

In the low power state, the battery cells of the device drain at a nominal rate (block 108). The drain may be due to current draw from some components of the device, the battery manager integrated circuit (which is still on), and cell self-discharge. The battery manager integrated circuit determines if a change is applied, such as recharging from a wall power source (block 110). If a charge is applied, the method 100 returns to block 102 where the device is in use. If a charge is not applied, the compares a level of the cell voltages to a threshold (block 114). If the voltage level of the cells is above the threshold, the method 100 returns to block 108 where the battery continues to experience nominal drain. When the voltage level of the batter cells falls below the threshold (e.g., a low voltage threshold), the battery manager integrated circuit disables power to avoid damaging the cells (block 114). Further, the battery output and the battery manager integrated circuit is turned off (block 116). At this point, the battery cells experience minimal drain (block 118). However, power is still drained from the battery in the form of self-discharge, with a significantly reduced drain from the battery manager integrated circuit and no drain from the device. At this time, the safe storage duration is shorter than is needed by a user. To exit this mode, a voltage must be applied to the battery manager from the device via an alternate power source. If a charge is not applied and the cell voltage of the battery drops below a minimum cell voltage (e.g., a minimum drain threshold) at which the battery is not capable of being charged, the battery manager disables charging, which effectively disables the pack permanently for safety.

If a charge is applied (block 120), the method 100 returns to block 102. If a charge is not applied, it is determined if any of the battery cells have a voltage level that is less than a minimum voltage threshold (block 122). If the battery cells have voltage levels that are greater than the minimum voltage threshold, the method 100 returns to block 120 to check if a charge has been applied. If at least one of the battery cells has a voltage that is less than the minimum voltage threshold, the battery back is permanently disabled since at this point the at least one battery cell is damaged and will not charge effectively (block 124). The method 100 then ends.

Figure 2:
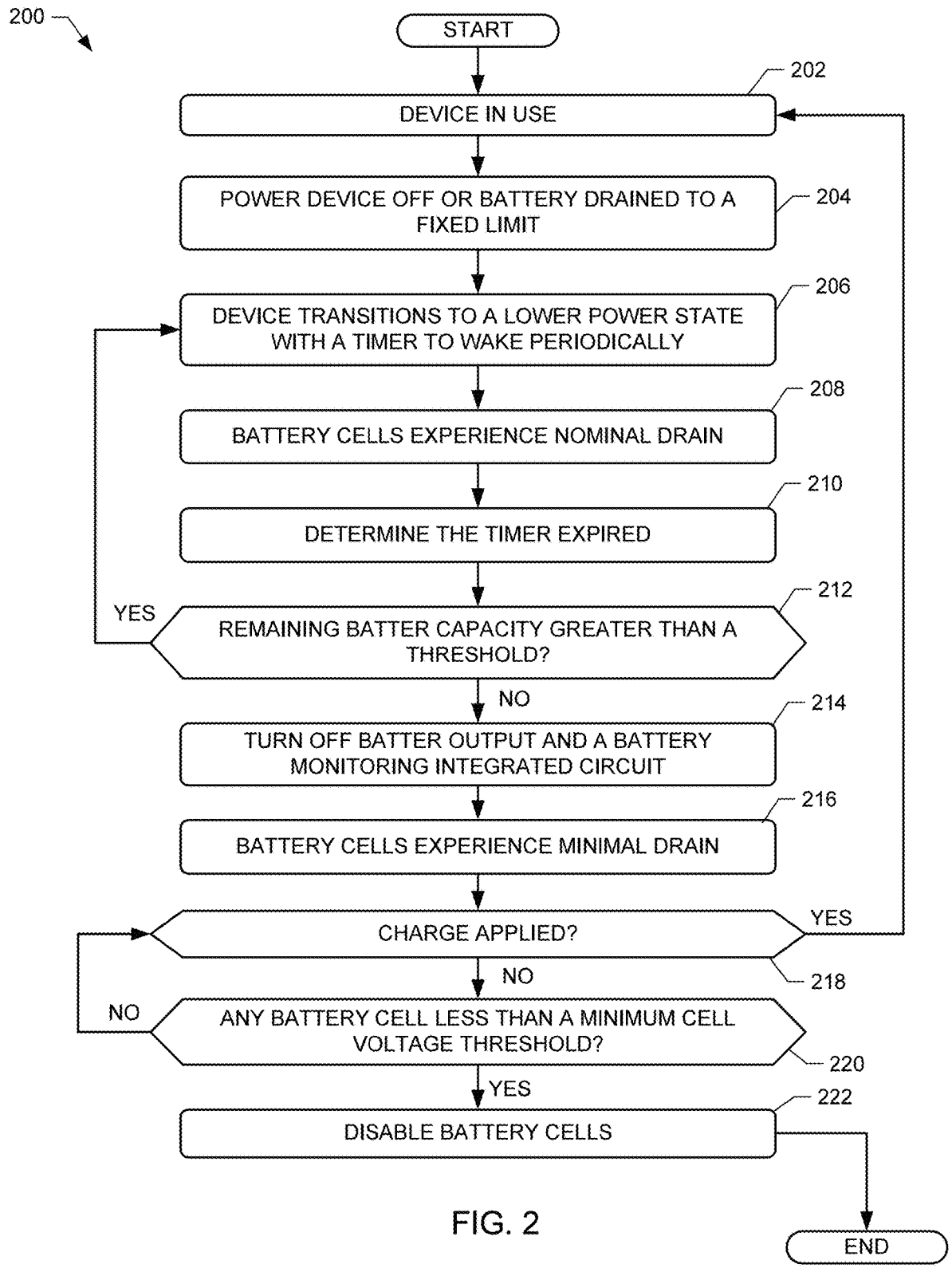
FIG. 2 is a flow chart illustrating a method for extending the storage life of a rechargeable battery according to an embodiment of the present disclosure.

FIG. 2 is a flow chart illustrating a method 200 for extending the storage life of a rechargeable battery, according to an embodiment of the present disclosure. While a device is in use (block 202), the device derives its power from the battery and is in communication with the battery. The communication method can include any serial, parallel or signal. At any time during the operation of the device, the user may manually power down the device by pressing the power button (block 204). Alternatively, the device powers off after the battery is drained to a fixed limit. Upon the device being manually powered down by the user, the battery output remains on and a computer implemented program run by the device transitions itself to a lower power state and initiates a timer set to expire after a predetermined length of time (block 206). In an embodiment, the predetermined length of the timer is approximately 12 hours. In another embodiment, the predetermined length of the timer is less than 12 hours. In another embodiment, the predetermined length of the timer is greater than 12 hours. For example, the predetermined length of the timer may be as short as 30 minutes and as long as 48 hours.

At this point, the battery cells experience nominal drain (block 208). The drain may be due to current draw from some components of the device, the battery manager integrated circuit (which is still on), and cell self-discharge. When the predetermined length of time expires and the timer terminates, the device commands itself to at least partially power on, out of its resting state (block 210). While in this state, the battery is drained by the device, the battery manager integrated circuit and self-discharge of the battery cell. In the timer triggered powered on state (e.g., a lower power mode), the device runs a query of the remaining capacity of the battery to determine if the remaining capacity of the battery is either greater than or less than a predetermined threshold (block 212). In an embodiment, the predetermined remaining capacity threshold is approximately less than 3.0 watt-hours (Wh). In another embodiment, the predetermined remaining capacity threshold is approximately 3.0 Wh. In yet another embodiment, the predetermined remaining capacity threshold is approximately greater than 3.0 Wh. For example, the predetermined remaining capacity threshold may be as low as 0.5 watt-hours and as great as 6.0 Wh.

If the query of the battery determines that the remaining capacity is less than or equal to the predetermined threshold, the battery is commanded to turn off all output and to turn off battery monitoring integrated circuits (block 214). In this state, the battery is being drained primarily through battery cell self-discharge with the battery manager integrated circuit load secondary and no pump load (block 216). To exit this mode, a voltage must be applied to the battery manager from the device via an alternate power source. If a charge is not applied and the cell voltage of the battery drops below a minimum cell voltage at which the battery is not capable of being charged, the battery manager disables charging, which effectively disables the pack permanently for safety.

If a charge is applied (block 218), the method 200 returns to block 202. If a charge is not applied, it is determined if any of the battery cells have a voltage level that is less than a minimum voltage threshold (block 220). If the battery cells have voltage levels that are greater than the minimum voltage threshold, the method 200 returns to block 218 to check if a charge has been applied. If at least one of the battery cells has a voltage that is less than the minimum voltage threshold, the battery back is permanently disabled since at this point the at least one battery cell is damaged and will not charge effectively (block 222). The method 200 then ends.

Returning to block 212, if the remaining capacity query determines that the remaining capacity of the battery is greater than or equal to the predetermined threshold, the device returns to the low power state until the timer expires again. The battery manager integrated circuit continues to monitor battery parameters. In this state the device can be powered on as normal by the user. If an alternate power source is applied to the device, it will turn on and charge the battery.

In some embodiments, the battery manager integrated circuit may have a cell under-voltage ("CUV") feature. However, in all cases the device will have turned off the battery manager and battery output before it reaches this threshold. Compared to the method 100, in the method 200 this lowest power consumption state begins earlier with more remaining capacity in the cells which prolongs the storage duration. This benefit is reduced if the user of the device drains the battery to the user limit. However there is still improvement in storage duration even in this extreme case.

Figure 3:
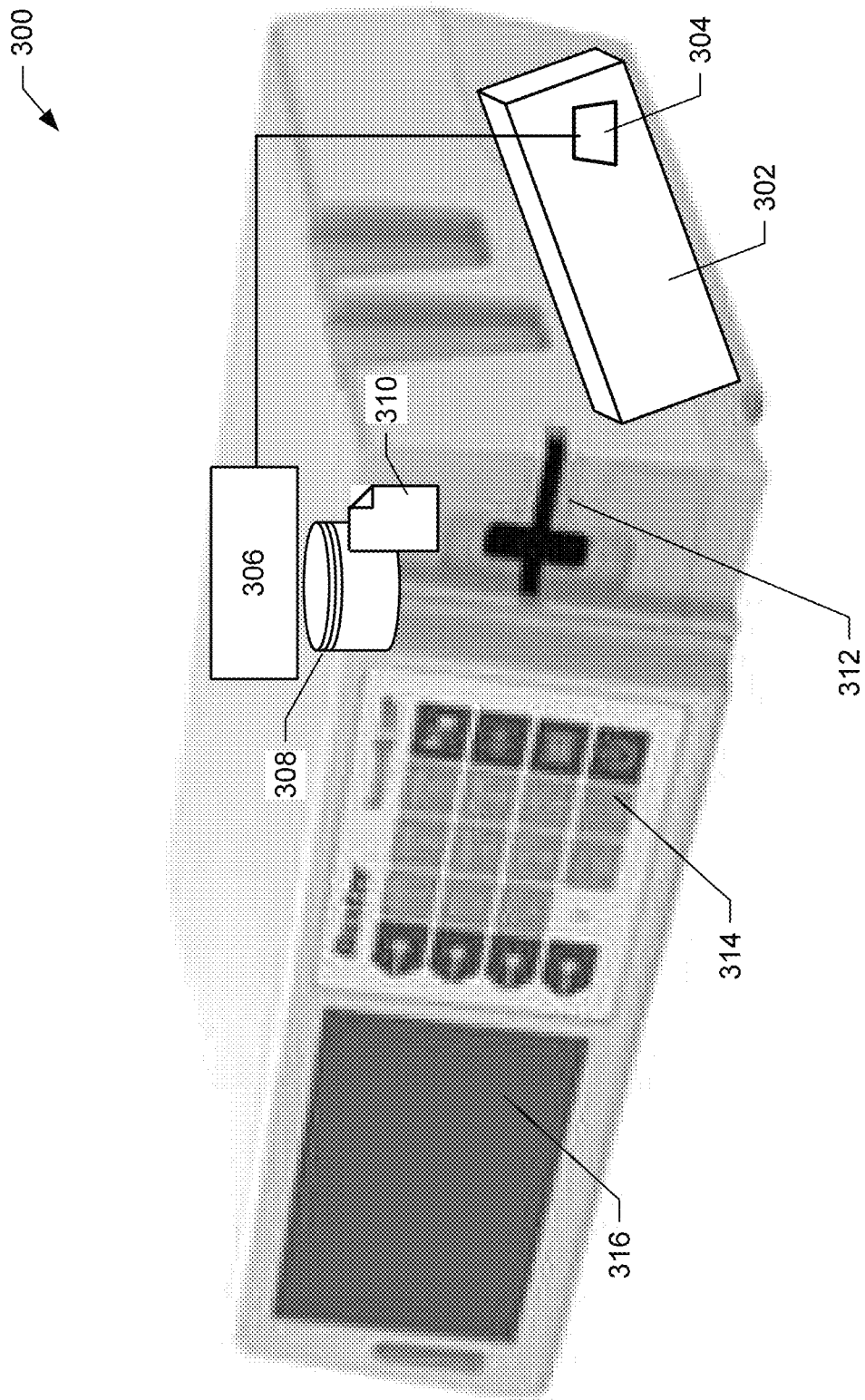
FIG. 3 is a diagram showing an example device configured to perform the method of FIG. 2, according to an example embodiment of the present disclosure.

FIG. 3 is a diagram showing an example device 300 configured to perform the method 200 of FIG. 2, according to an example embodiment of the present disclosure. The device 300 may be an infusion pump, a dialysis machine, or other medical device. The infusion pump in various embodiments is a peristaltic pump, a syringe pump, or an ambulatory pump configured to deliver a medication to a patient. It should be appreciated that the device 300 is in various embodiments, may include any type of medical device, or any other suitable device having a rechargeable battery.

The device 300 of FIG. 3 includes a rechargeable battery 302 having one or more battery cells. The rechargeable battery 302 may include battery manager electronics 304 for monitoring current and/or voltage levels of the battery cells. The battery manager electronics 304 may also disable the rechargeable battery 302 when at least a voltage level of one of the cells falls below a minimum voltage threshold. In some embodiments, the battery manager electronics 304 may include the battery manager integrated circuit discussed in conjunction with FIG. 2.

The device 300 also includes a computing unit 306 and a memory device 308. The computing unit 306 may include a processor, application specific integrated circuit, microcontroller, logic controller, etc. The memory device 308 includes any solid state or flash drive. The memory device 308 includes a computer implemented program 310 (e.g., computer-readable instructions) that is executable by the computing unit 306 to perform at least the method 200 of FIG. 2. In some embodiments, the battery manager electronics 304 may be included within the computing unit 306.

The computing unit 306 may also control operation of the device 300. For example, the computing unit 306 controls one or more pumps or valves in an actuation area 312 that operate on an intravenous tube to pump a fluid or a drug from a container to a patient. The device 300 also includes an interface 314, such as buttons including a power on/off button. The interface 314 is configured to receive user-specified commands for the device 300. The device 300 may also include a display screen 316 for showing information related to an operation of the device 300 or a treatment provided by the device 300. The display screen 316 may include a touchscreen.

In one embodiment, the infusion pump device 300 has the following states: a device active state that consumes 4 W, a device shutdown state that consumes 30 mW, and a battery shutdown state that consumes 250 uW. In one embodiment, the device battery 302 has the following states: a device usable state having a capacity above 0 Wh, a reserved capacity state having a capacity between 0 Wh to −1.0 Wh, and cell protection state (permanently disabled) that is below −1.9 Wh of remaining capacity.

Under the current known method 100 shown in FIG. 1, if a user is allowed to deplete the battery at 4 W per hour to a remaining capacity of 0 Wh, the device will then transition to the device shutdown state for approximately 1.4 days, this is followed by the battery transitioning to the battery shutdown state for approximately 150 days. Under the new disclosed method 200 shown in FIG. 2, in the worst case the user is allowed to deplete the battery at 4 W per hour to a remaining capacity of 0 Wh. The device will then transition directly to battery shutdown state for approximately 317 days based on self-discharge. Under the new disclosed method 200 shown in FIG. 2, in the best case the user will manually turn the device off with greater than 3 Wh remaining. The device 300 will then transition directly to the battery shutdown state for approximately 817 days based on self-discharge. It should be appreciated that other limiting factors unrelated to over-discharge may limit actual storage time to approximately 2 years.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A battery control method for extending a storage lifetime of a rechargeable battery in a device, the method comprising:
providing a device that derives its power from the rechargeable battery, wherein the device includes a computing unit capable of executing a computer implemented program, and wherein the rechargeable battery is capable of communicating with the device;
deploying the computer implemented program on the device in which the computing unit of the device commands the rechargeable battery to enter a lower power state after the device is manually powered down by user;
automatically powering up the device into a low power mode from the lower power state after expiration of a variable duration timer that triggers the computing unit to evaluate a state of charge of the rechargeable battery and continuously repeats according to a programed duration cycle;
evaluating the state of charge of the rechargeable battery, via the rechargeable battery and/or the computing unit, when the device is powered in the low power mode;
determining whether the a remaining capacity of the rechargeable battery is above or below a variable programed threshold using the state of charge;
communicating a command to the rechargeable battery to remain in an off or low power state until a charge is applied to the rechargeable battery after determining the remaining capacity of the rechargeable battery is below the variable programed threshold; and
waking the device and the rechargeable battery after detection of an alternate power source.

2. The method of claim 1, wherein the variable duration timer has a predetermined length that is 12 hours.

3. The method of claim 1, wherein the variable duration timer has a predetermined length that is between thirty minutes and 48 hours.

4. The method of claim 1, wherein the variable programed threshold is 3.0 watt-hours ("Wh").

5. The method of claim 1, wherein the variable programed threshold is between 0.5 Wh and 6.0 Wh.

6. The method of claim 1, further comprising:
detecting, via the computing unit, that at least one cell of the rechargeable battery is below a minimum cell voltage; and
causing the rechargeable battery to disable.

7. The method of claim 6, wherein the minimum cell voltage is corresponds to −1.9 Wh of remaining capacity of the rechargeable battery.

8. An apparatus with battery control for extending a storage lifetime of a rechargeable battery, the apparatus comprising:
a rechargeable battery having one or more battery cells;
a user interface; and
a computing unit communicatively coupled to the user interface and the rechargeable battery, the computing unit configured to execute a computer implemented program that causes the computing unit to:
command the rechargeable battery to enter a lower power state after receiving a command via the user interface to manually power down,
automatically power into a low power mode from the lower power state after expiration of a variable duration timer that triggers the computing unit to evaluate a state of charge of the rechargeable battery and continuously repeats according to a programed duration cycle,
evaluate the state of charge of the rechargeable battery when the computing unit is powered in the low power mode, determine whether a remaining capacity of the rechargeable battery is above or below a variable programed threshold using the state of charge, communicate a command to the rechargeable battery to remain in an off or low power state until a charge is applied to the rechargeable battery after determining the remaining capacity of the rechargeable battery is below the variable programed threshold, and wake the rechargeable battery after detection of an alternate power source.

9. The apparatus of claim 8, wherein the rechargeable battery, the user interface, and the computing unit are part of a peristaltic pump, a syringe pump, or an ambulatory pump.

10. The apparatus of claim 8, wherein the variable duration timer has a predetermined length that is between thirty minutes and 48 hours.

11. The apparatus of claim 8, wherein the variable programed threshold is between 0.5 Wh and 6.0 Wh.

12. The apparatus of claim 8, wherein the computer implemented program is further configured to cause the computing unit to:

detect that at least one cell of the rechargeable battery is below a minimum cell voltage; and cause the rechargeable battery to disable.

13. The apparatus of claim 12, wherein the minimum cell voltage is corresponds to −1.9 Wh of remaining capacity of the rechargeable battery.

14. The apparatus of claim 8, wherein the computing unit manages a device active state that is configured to consume 4 W, and wherein the low power mode consumes 30 mW and the off or low power state consumes 250 uW.

15. The apparatus of claim 14, wherein the off or low power state is a battery shutdown state.

16. The apparatus of claim 8, wherein the computer implemented program is configured to at least double a storage life of the rechargeable battery using the variable duration timer and by placing the rechargeable battery into the off or low power state after determining the remaining capacity of the rechargeable battery is below the variable programed threshold.

17. An apparatus with battery control for extending a storage lifetime of a rechargeable battery, the apparatus comprising:

a user interface; and a computing unit communicatively coupled to the user interface and a rechargeable battery, the computing unit configured to execute a computer implemented program that causes the computing unit to:

command the rechargeable battery to enter a lower power state after receiving a command via the user interface to manually power down, automatically power into a low power mode from the lower power state after expiration of a variable duration timer that triggers the computing unit to evaluate a state of charge of the rechargeable battery and continuously repeats according to a programed duration cycle, evaluate the state of charge of the rechargeable battery when the computing unit is powered in the low power mode, determine whether a remaining capacity of the rechargeable battery is above or below a variable programed threshold using the state of charge, communicate a command to the rechargeable battery to remain in an off or low power state until a charge is applied to the rechargeable battery after determining the remaining capacity of the rechargeable battery is below the variable programed threshold, and wake the rechargeable battery after detection of an alternate power source.

18. The apparatus of claim 17, wherein the user interface and the computing unit are part of a peristaltic pump, a syringe pump, or an ambulatory pump.

19. The apparatus of claim 17, wherein the variable duration timer has a predetermined length that is between thirty minutes and 48 hours, and wherein the variable programed threshold is between 0.5 Wh and 6.0 Wh.

20. The apparatus of claim 17, wherein the computer implemented program is further configured to cause the computing unit to:

detect that at least one cell of the rechargeable battery is below a minimum cell voltage; and cause the rechargeable battery to disable.

* * * * *